United States Patent
Erhard et al.

(10) Patent No.: US 9,993,223 B2
(45) Date of Patent: Jun. 12, 2018

(54) INDIVIDUAL MONITORING OF COMPRESSION FOR MAMMOGRAPHIC EXAMINATIONS

(71) Applicant: KONINKLIJKE PHILIPS N.V., Eindhoven (NL)

(72) Inventors: Klaus Erhard, Hamburg (DE); Hanns-Ingo Maack, Norderstedt (DE); Andreas Loeprich, Ebersdorf (DE); Nataly Wieberneit, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 998 days.

(21) Appl. No.: 14/359,294

(22) PCT Filed: Nov. 14, 2012

(86) PCT No.: PCT/IB2012/056405
§ 371 (c)(1),
(2) Date: May 19, 2014

(87) PCT Pub. No.: WO2013/076622
PCT Pub. Date: May 30, 2013

(65) Prior Publication Data
US 2014/0328458 A1 Nov. 6, 2014

Related U.S. Application Data

(60) Provisional application No. 61/562,134, filed on Nov. 21, 2011.

(51) Int. Cl.
*A61B 6/04* (2006.01)
*A61B 6/00* (2006.01)
*G01L 1/26* (2006.01)

(52) U.S. Cl.
CPC ............ *A61B 6/548* (2013.01); *A61B 6/0414* (2013.01); *A61B 6/502* (2013.01); *G01L 1/26* (2013.01)

(58) Field of Classification Search
CPC .............................. A61B 6/502; A61B 6/0414
See application file for complete search history.

(56) References Cited

U.S. PATENT DOCUMENTS 5,335,257 A * 8/1994 Stunberg ................ A61B 6/502
378/117
7,656,993 B2 2/2010 Hoernig
(Continued)

FOREIGN PATENT DOCUMENTS

JP 2009285345 12/2009
JP 2011206434 A 10/2011
(Continued)

*Primary Examiner* — Hoon Song
(74) *Attorney, Agent, or Firm* — Larry Liberchuk (57) ABSTRACT

The present invention relates to mammography. In particular, the present invention relates to a method and a corresponding system for individually monitoring a compression force in an apparatus for mammographic examination for personalized compression guidance. In order to provide a personalized guidance for the compression of the breast in a first step (S1a, S1b, S1c) a breast contact area (A) between a breast under examination and a compression plate (3) or a support plate (15) is determined. In a next step (S5) a compression force limit is determined based on the breast contact area (A). Then, in a further step (S9a, S9b, S9c) an output signal (5) representative of the relation between the breast contact area (A) and the compression force limit is provided to a user such that the user may decide whether to complete or to continue the application of compression force.

16 Claims, 7 Drawing Sheets

(56) References Cited

U.S. PATENT DOCUMENTS

2009/0262887 A1 10/2009 Iordache et al.
2013/0028373 A1* 1/2013 Den Heeten ........... A61B 6/502
378/37

FOREIGN PATENT DOCUMENTS

WO 2011102713 A1 8/2011
WO WO2011102713 8/2011

* cited by examiner

| A | I | II | III | V | IV | VI |
|---|---|---|---|---|---|---|
| 36 | 100 | 36 | 60 | 1 | 2,8 | 1,7 |
| 72 | 100 | 72 | 90 | 1 | 1,4 | 1,3 |
| 144 | 100 | 144 | 120 | 1 | 0,7 | 0,8 |
| 288 | 100 | 200 | 150 | 0,694 | 0,3 | 0,5 |
| 576 | 100 | 200 | 180 | 0,347 | 0,2 | 0,3 |
| 720 | 100 | 200 | 200 | 0,278 | 0,1 | 0,3 |

INDIVIDUAL MONITORING OF COMPRESSION FOR MAMMOGRAPHIC EXAMINATIONS

CROSS-REFERENCE TO PRIOR APPLICATIONS

This application is the U.S. National Phase application under 35 U.S.C. § 371 of International Application Serial No. PCT/IB2012/056405, filed on Nov. 14, 2012, which claims the benefit of U.S. Application Ser. No. 61/562,134, filed on Nov. 21, 2011. These applications are hereby incorporated by reference herein.

FIELD OF THE INVENTION

The present invention relates to mammography. In particular, the present invention relates to a method and a corresponding system for individually monitoring a compression force in an apparatus for mammographic examination for personalized compression guidance. Furthermore, the present invention relates to a computer program element and a computer readable medium.

BACKGROUND OF THE INVENTION

Mammography information is used for example for breast cancer screening. During mammography a breast under examination is mechanically compressed and subsequently a radiographic image of the flattened breast tissue is acquired. The mechanical compression of the breast prevents motion artefacts in the images. Moreover, the compression helps to obtain a homogeneous breast tissue thickness and to spread breast structures.

The compression is usually controlled by a compression force which may for example be equal for each patient. According to the European Guidelines for Quality Assurance in Breast Cancer Screening and Diagnosis (N. Perry et al. 2006, 4th edition, Office for the Official Publications of the European Communities, Luxembourg) a maximal compression force between 130 and 200 N is suggested.

U.S. Pat. No. 5,335,257 suggests a compression control in which the compression depends on a compression height of the breast under examination. The compression force is increased as long as the compression height decreases, i.e. as long as the breast is still pliable. However, the compression often causes discomfort.

SUMMARY OF THE INVENTION

Thus, there may be a need to provide a method and a system which provides a personalized guidance for the compression of the breast.

The object of the present invention is solved by the subject-matter of the independent claims. Further exemplary embodiments are evident from the dependent claims and the following description.

According to a first aspect of the present invention a method for individually monitoring a compression force in an apparatus for mammographic examination is provided. The method comprises the following steps: determining a breast contact area between a breast under examination and a compression plate; determining a compression force limit based on the breast contact area; providing an output signal representative of the relation between the breast contact area and the force limit.

In other words the idea of the invention may be seen in providing a feedback which allows a user to control the compression force depending on the breast size and in particular depending on the breast contact area of the person under examination. The breast contact area is determined indirectly by estimating the breast size or directly by actually measuring the breast contact area. The corresponding compression force limit is calculated according to a pressure-force optimization rule, i.e. the compression force is computed as a function of the breast contact area. Furthermore, the output signal indicates for example visually or acoustically whether the currently applied compression force is appropriate for the breast under examination.

According to an exemplary embodiment of the invention the compression force limit is proportional to one of the following mathematical functions or combinations thereof: a logarithm of the breast contact area, an exponential function of the breast contact area, a power function of the breast contact area or a linear function of the breast contact area.

According to a further exemplary embodiment of the invention the breast contact area is determined by estimating the breast size by a user before the compression of the breast.

According to a further exemplary embodiment of the invention the breast contact area is determined automatically in real-time during the compression of the breast.

According to a further exemplary embodiment of the invention the output signal is an optical and/or an acoustical signal.

According to a further exemplary embodiment of the invention the acoustical signal varies in frequency and/or tone depending on the breast size correlated to the compression force limit.

According to a second aspect of the present invention a system for individually monitoring a compression force during a mammographic examination is provided. The system comprises a support plate for supporting a breast while radiographic images are obtained and a moveable compression plate for compressing the breast between the support plate and the compression plate while the radiographic images are obtained. Furthermore, the system comprises a monitoring device for monitoring a compression force applied to the breast. The monitoring device is adapted for determining a breast contact area between the breast and the compression plate or between the breast and the support plate. Furthermore, the monitoring device is adapted for determining a compression force limit based on the determined breast contact area. Moreover, the monitoring device is adapted for providing an output signal representative of the relation between the breast contact area and the force limit.

According to an exemplary embodiment of the invention the system further comprises a tracking device for measuring the breast contact area in real time and for providing the measured breast contact area to the monitoring device.

It has to be noted that features described with respect to the method for individually monitoring a compression force in an apparatus for mammographic examination as described above and in the following may be features of the system and vice versa.

These and other aspects of the invention will be apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
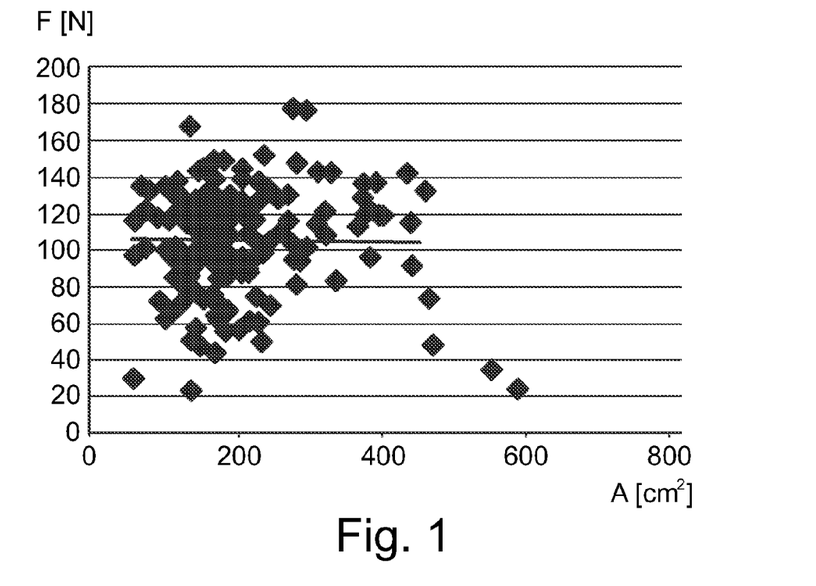
FIG. 1 shows a graph representing a compression force and the corresponding breast contact area resulting from a known compression technique

In FIG. 1 a graph is shown in which a known technique of applying a compression force during mammographic examination is represented. According to this technique the compression force depends on a compression height of the breast, i.e. on a distance between two plates between which the breast is positioned. The compression force is increased as long as the compression height of the breast decreases, i.e. as long as the breast is still pliable.

Figure 2:
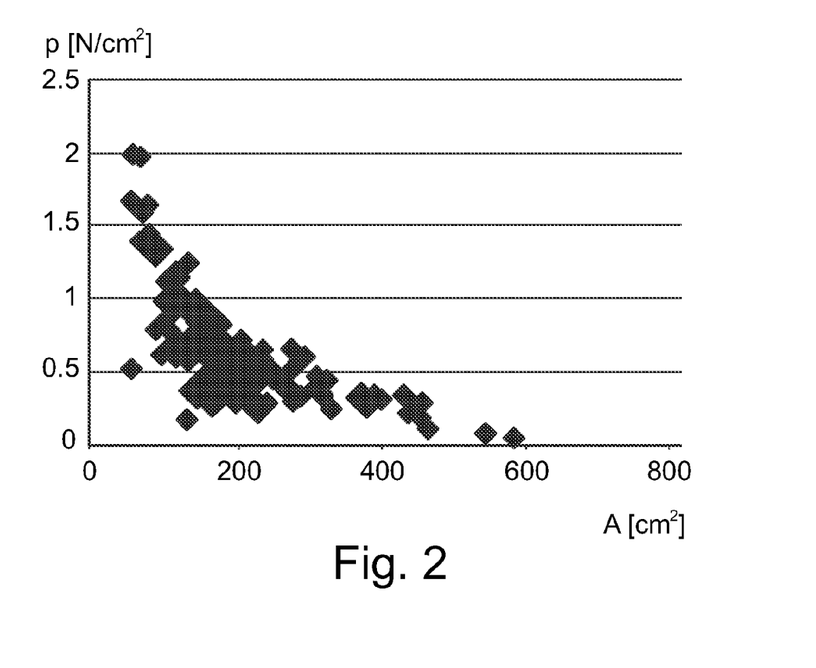
FIG. 2 shows a graph representing a compression pressure corresponding to the force values of FIG. 1

The compression causes pain sensations for the person under examination and leads to a reduced readiness to participate in mammographic screenings. The pain sensation may vary from person to person. FIG. 1 and FIG. 2 may partially explain the different pain sensations.

The graph in FIG. 1 shows the results of such a compression control which depends on the experience and subjective decisions of a user such as an assistant medical technician (AMT) or a radiology assistant. The y-axis shows the compression force F in Newton (N) and the x-axis shows the breast size represented as a breast contact area A in square centimeters ($cm^2$). Each dot represents the final compression force value and the corresponding breast area value at the end of the compression procedure for a respective person.

FIG. 2 shows the compression pressure p corresponding to the values of FIG. 1. In FIG. 2 the y-axis represents the compression pressure p in Newton per square centimeter ($N/cm^2$) and the x-axis shows the breast size as in FIG. 1. As may be seen from FIGS. 1 and 2 the known technique leads to a very high compression pressure for small breasts. Thus, smaller breasts experience a higher local pressure at the same compression force as larger breasts. This causes intensive pain sensations, particularly for persons with small breasts.

Figure 3:
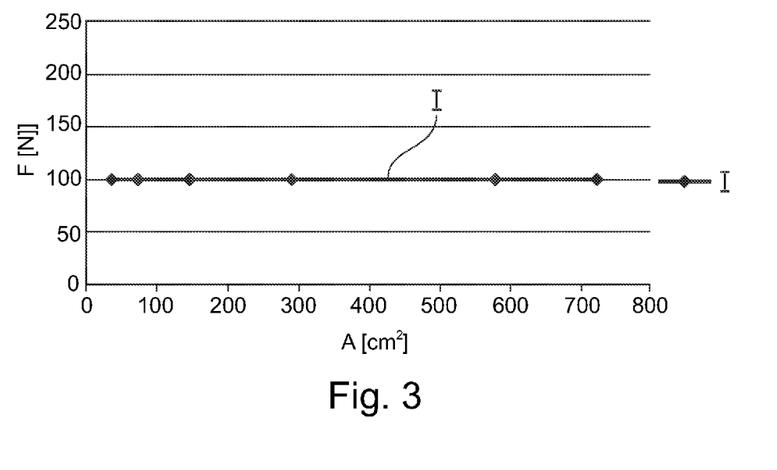
FIG. 3 shows a graph representing a known compression technique with a fixed compression force

FIG. 3 shows the results of a further known compression technique in which a fixed compression force of for example 100 N is applied to each person. In other words a "one-fits-all-force" is applied. As in FIG. 1 the y-axis shows the compression force F and the x-axis shows the breast size. The curve representing the fixed compression force is denoted with I.

Figure 4:
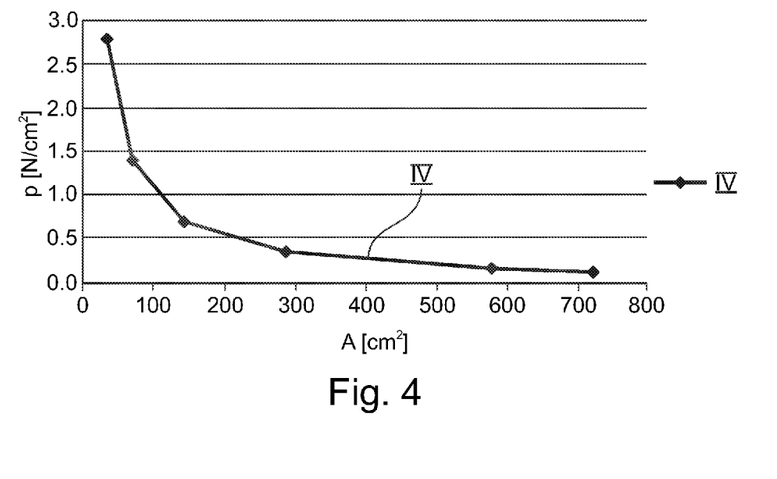
FIG. 4 shows a graph representing a compression pressure corresponding to the force values of FIG. 3

FIG. 4 shows the compression pressure p corresponding to the values of FIG. 3. As in FIG. 2 the y-axis represents the compression pressure p and the x-axis shows the breast size. The curve representing the compression pressure p in FIG. 4 is denoted with IV. Similar to the technique described with respect to FIGS. 1 and 2 the compression with a fixed compression force causes intensive pain sensations, particularly for persons with small breasts. Large breasts on the other hand may get a compression which does not guarantee an optimal image quality of the mammography examination.

Contrary to the known techniques as in FIGS. 1 to 4 where the maximal compression force applied is not correlated to the breast size or to the breast contact area, the method and system according to embodiments of the invention consider the breast size and thus the pressure exerted on the breast.

Figure 5:
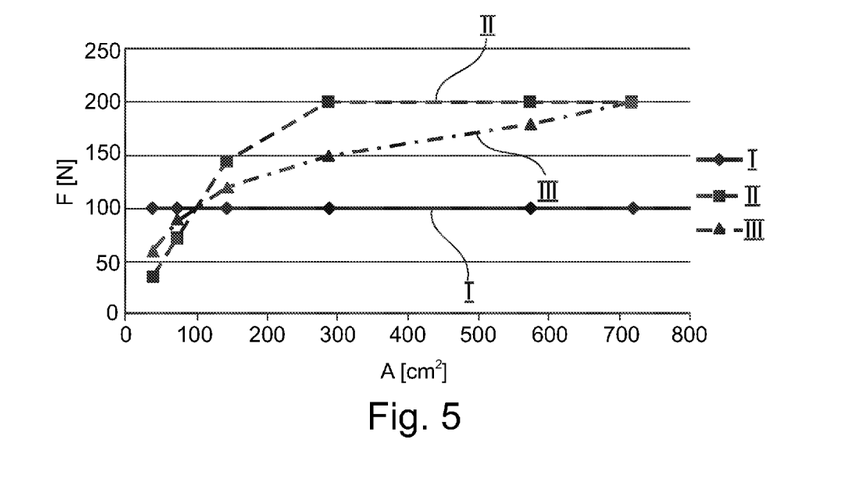
FIG. 5 schematically shows a graph representing a compression force optimization depending on the breast contact area according to an embodiment of the invention FIG. 6 schematically shows a graph representing a compression pressure corresponding to the force values of FIG. 5

FIG. 5 schematically shows a graph representing a compression force optimization depending on the breast contact area A according to an embodiment of the invention. As in FIGS. 1 and 3 the y-axis shows the compression force F and the x-axis shows the breast contact area A. The curves represent a compression force F, particularly a maximal compression force also denoted as a compression force limit for each breast contact area.

A curve denoted as curve II represents an application of compression force such that constant compression pressure which depends on the breast contact area is exerted on the breast. However, the maximal compression force is limited for regulatory reasons at 200 N. Moreover, a curve denoted as curve III represents an application of compression force such that the compression force limit is directly proportional to a mathematical function of the breast contact area such as a logarithm. For comparison, a curve denoted as curve I is included which represents an application of constant force independent from the breast contact area as already shown in FIG. 3.

According to an embodiment of the invention the compression force limit for each breast size or for each breast contact area is chosen such that it lies between curve I and curve II. This is for example fulfilled for curve III. Therein, the compression force limit may lie in the range of 100 N to 200 N. Compared to curve I with a fixed compression force limit curve III may allow smaller compression force limits for small breasts and larger compression force limits for larger breasts.

According to an embodiment of the invention the compression force limit may be determined by a compression force optimization rule.

According to a further embodiment of the invention the compression force limit F is proportional to a mathematical function or combinations of mathematical functions, wherein the mathematical functions are dependent on the breast contact area A. Particularly, the compression force limit may be proportional to a logarithm of the compression area:

$$F(A) \sim a * \log(A) + b$$

Moreover, the compression force limit may be proportional to a linear function of the breast contact area:

$$F(A) \sim a*A + b$$

Furthermore, the compression force limit may be proportional to a power function of the breast contact area:

$$F(A) \sim a*A^b + c$$

According to a further embodiment the compression force limit may be proportional to an exponential function of the breast contact area:

$$F(A) \sim a*\exp(b*A) + c$$

Figure 11:
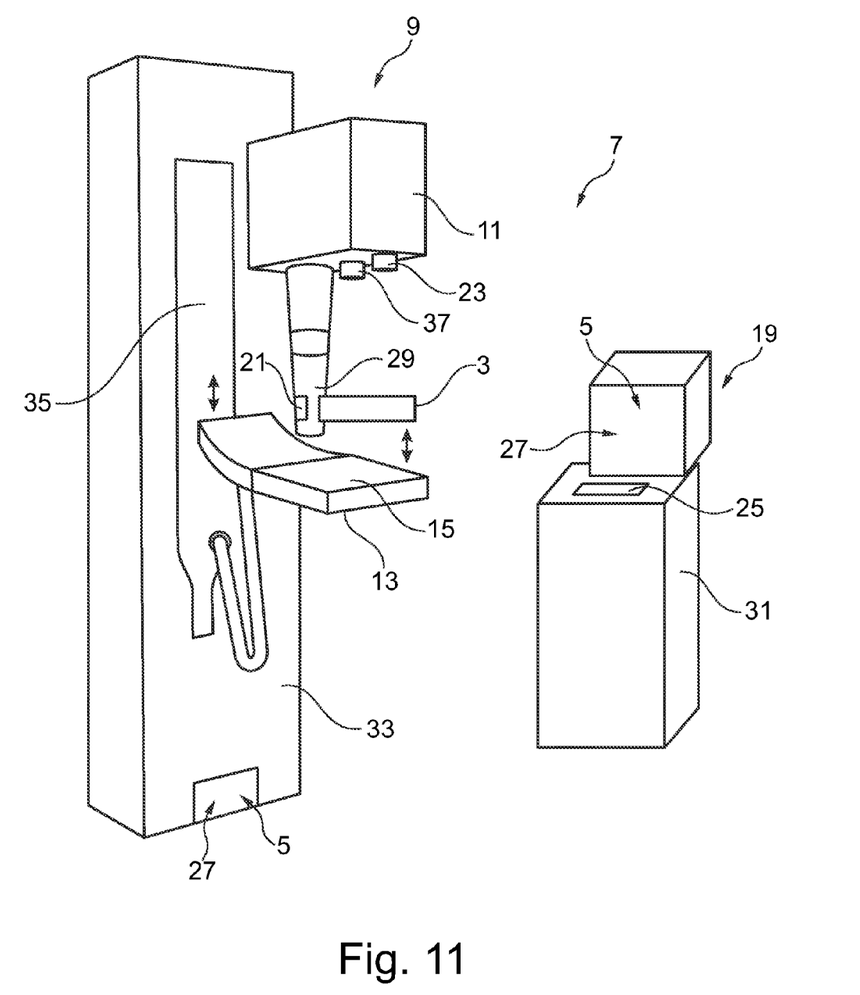

Moreover, the compression force limit may be proportional to any combination of the mathematical functions mentioned above. Therein, "a", "b" and "c" may denote constants. According to a further embodiment of the invention a table with different values for constants "a", "b" and "c" may be stored on a memory of a processing unit 31 (as shown in FIG. 11). These values may be adapted by a user according to clinical praxis and experience. Alternatively, the values for "a", "b" and "c" may be entered manually by a user in the beginning of the compression procedure.

According to a further embodiment of the invention the curve representing the compression force limit $F(A)$ may be monotonically increasing. Moreover, the curve $F(A)$ may have an upper limit, e.g. $F_{upper\ limit}$. Furthermore, the curve $F(A)$ may have a lower limit, e.g. $F_{lower\ limit}$.

According to a further embodiment of the invention the compression force limit may be determined with the help of the following equation:

$$F(A) = (F_{upper\ limit} - F_{lower\ limit})*(1 - \exp(-c*A)) + F_{lower\ limit}$$

Therein, $F_{upper\ limit}$ may represent a maximal compression force limit which should not be trespassed independently of the breast size. For example, $F_{upper\ limit}$ may be 200 N as shown in FIG. 5. Moreover, $F_{lower\ limit}$ may represent a minimal compression force of for example 50 N. $F_{upper\ limit}$ and $F_{lower\ limit}$ may for example be derived from a table for example stored in a memory of a processing unit 31 (as shown in FIG. 11). Alternatively, $F_{upper\ limit}$ and $F_{lower\ limit}$ may be entered manually by a user in the beginning of the compression procedure.

Figure 14:
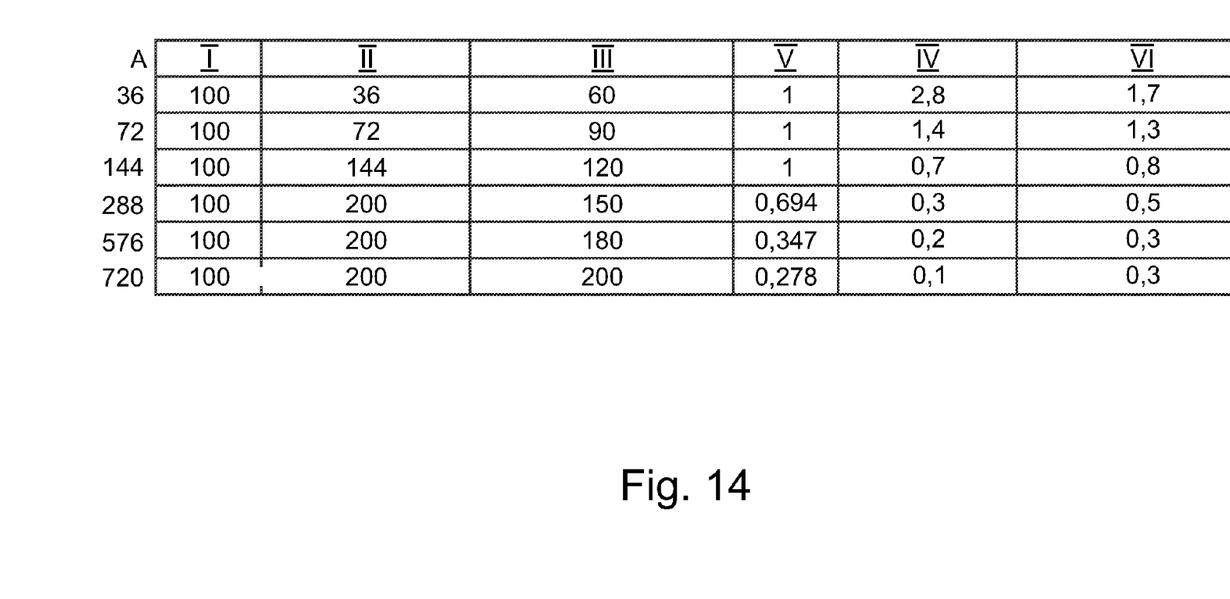
FIG. 14 shows a table with values for compression force limits and compression pressures corresponding to different breast contact areas

According to a further embodiment of the invention single values for a compression force limit for each breast size category are saved on a memory, e.g. on a memory of the processing unit 31 (in FIG. 11). Thus, after determining a breast size category the corresponding value may be derived for example automatically e.g. from a table. In this embodiment no calculation of the compression force limit is necessary. A corresponding table is shown in FIG. 14. The table comprises discrete force or pressure values for the different curves I to VI shown in FIGS. 3 to 6.

According to a further embodiment of the invention the values of the compression force limit may be tuned, i.e. adapted or replaced by a user.

Figure 6:
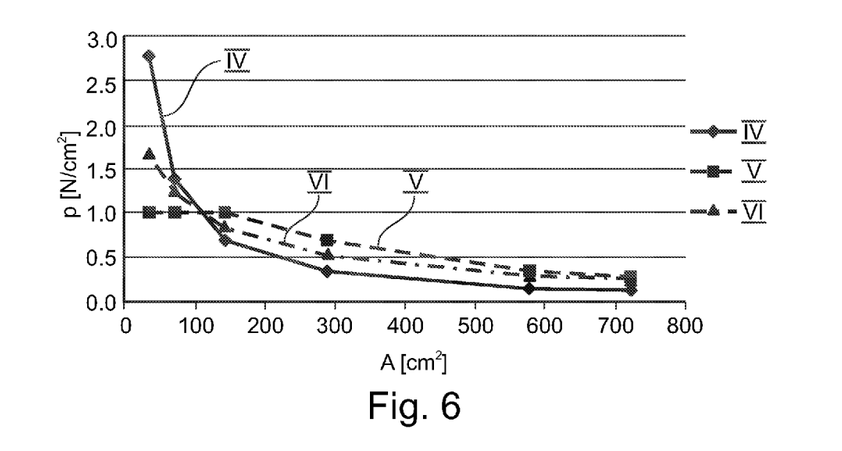

FIG. 6 shows the compression pressure p for each of the curves shown in FIG. 5. As in FIGS. 2 and 4 the y-axis represents the compression pressure p and the x-axis shows the breast contact area A. The maximal pressure for each breast size is represented for the force values of each curve in FIG. 5 with the corresponding symbols (diamonds, squares and triangles). Therein, curve IV represents the pressure p with a fixed compression force application. Curve V represents a fixed pressure p application and curve VI represents a pressure p when the compression force is applied such that the compression force limit is directly proportional to a mathematical function such as a logarithm. As may be seen in FIG. 6 the extreme pressure for small breasts is avoided in comparison to a fixed compression force limit. Furthermore, large breasts get a greater compression pressure as compared to the fixed compression force limit.

Figure 7:
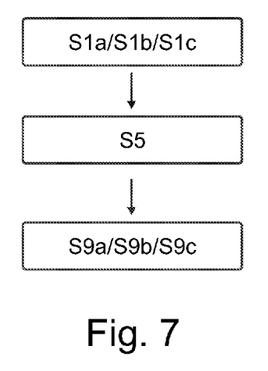
FIG. 7 schematically shows basic steps of a method for individually monitoring a compression force according to an embodiment of the invention FIG. 8 schematically shows a further embodiment of a method according to the invention FIG. 9 schematically shows a further embodiment of a method according to the invention FIG. 10 schematically shows a further embodiment of a method according to the invention FIG. 11 schematically shows a system for individually monitoring a compression force during a mammographic examination according to an embodiment of the invention

FIG. 7 shows the application of the idea explained with respect to FIGS. 5 and 6 in a method for individually monitoring and/or controlling a compression force according to an embodiment of the invention. In a first step S1a, S1b or S1c a breast contact area between a breast under examination or to be examined and a compression plate or a support plate is determined. Therein, the breast contact area may denote an area of a breast which is in physical contact with a compression plate or a support plate of an apparatus for mammographic examination. The compression plate and the support plate may for example be provided as paddles.

The breast contact area may be determined by visually estimating (step S1a) a breast size category, by estimating (step S1b) the breast size category in a pre-compressed state of the breast with the help of visual markers 17 (FIG. 13) or by directly measuring (step S1c) the breast contact area between the compression plate and the breast. Therein, the breast size or breast size category is directly correlated to the breast contact area. E.g. the larger a breast, the larger also the breast contact area and vice versa.

The breast contact area may furthermore depend on elastic properties of the breast. E.g. the less elastic a breast, the smaller is the breast contact area. Thus, the breast contact area may depend on the size and elasticity of a breast.

After determining the breast contact area a compression force limit based on the breast contact area is determined in a subsequent step S5. For determining the compression force limit compression force optimization rules may be applied as for example described in connection with FIGS. 5 and 6. The compression force limit may denote a maximal compression force applicable to a certain breast contact area or breast size category such that an optimal pressure is exerted on the breast. The compression force limit may be determined continuously, i.e. for each possible breast contact area as shown in the second curve of FIG. 5. Alternatively, the compression force limit may be determined discretely, i.e. one compression force limit value for each breast size category.

In a further step S9a, S9b or S9c an output signal representative of the relation between the breast contact area and the compression force limit is provided to a user as a feedback. For example, the output signal may be an optical and/or an acoustical signal. The optical signal may include varying colors such as green when the force applied during the mammography examination is under the compression force limit determined in step S5 and red when the force applied exceeds the determined compression force limit. Moreover, the optical signal may provide indicators on a screen such as numbers or words. For example, the terms "low", "ok" and/or "high" may be displayed on a screen depending on the determined breast contact area, the determined compression force limit and the compression force currently applied to the breast. Alternatively, the output signal may show on a display for which breast size the currently applied compression force fits or is acceptable.

An acoustic signal could comprise a varying frequency or a varying tone. For example, if the applied force is approaching the compression force limit for a determined breast size category, the frequency and/or the tone may increase. Moreover, the output signal may be provided continuously e.g.

visually. Alternatively, the output signal may be provided only when the compression force limit is reached, e.g. acoustically. The different possibilities of providing the output signal will be explained in more detail with respect to FIGS. 8 to 12.

By determining the breast contact area and deriving a compression force limit based on the breast contact area it is possible to provide a possibility for optimizing and controlling the breast compression during mammography examinations. The optimization may result in a beneficial compromise between image quality and pain sensation. An extreme application of force on small breasts may be avoided and thus pain sensations may be reduced. The reduction in pain due to a personalized compression force may lead to more comfort during the mammography examination. Thus, it may lead to a better acceptance of mammography and may increase a participation rate in screening programs. Moreover, large breasts may be compressed more than in known techniques such that a better image quality may be achieved.

Figure 8:
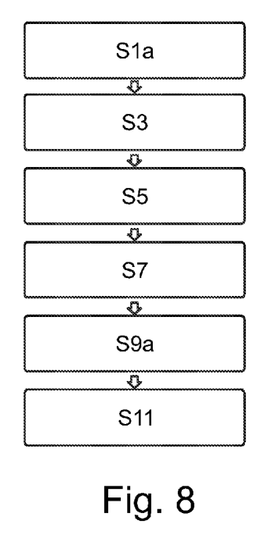
Figure 9:
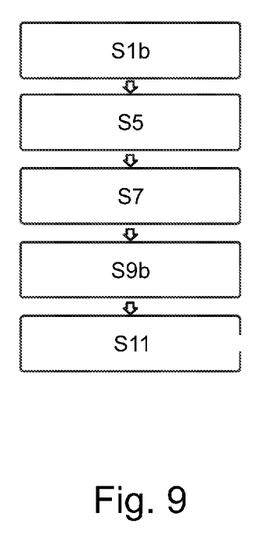
Figure 10:
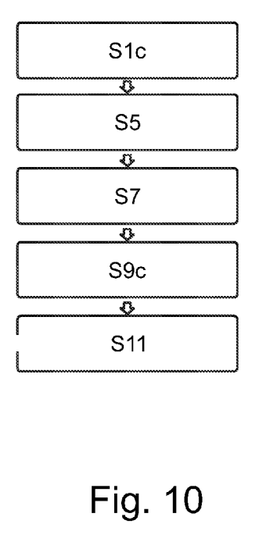

FIGS. 8 to 10 show further embodiments of a method according to the invention. In FIG. 8 a breast contact area is determined by estimating the breast size in a first step S1a. Therein, a user such as an AMT may determine the breast size also denoted as breast size category visually. The breast size may for example be determined by 4 or 5 cup sizes such as A for small to E for very large as shown in detail in FIG. 13. Subsequently, the estimated breast size is provided to the mammography system (step S3) with the help of an interaction device 25 such as a keyboard (as shown in FIG. 11). For example, the AMT may enter the estimated breast size category with the help of buttons positioned near a display 27 (FIG. 11). The mammography system 7, and particularly a monitoring device 19 (FIG. 11) determines a compression force limit based on the breast contact area as described above (step S5). Subsequently, the AMT may initiate a compression of the breast in step S7. For example, this may be done by activating a foot pedal or a button. After the start of the compression an output signal is provided in step S9a. The output signal indicates on a display whether the applied compression force is low, ok or high for the entered breast size. I.e. the output signal shows whether the applied compression force is lower or higher than the determined compression force limit. In a further step S11 the AMT decides to complete or to continue the compression of the breast.

The embodiment of the method described in FIG. 9 is similar to the embodiment in FIG. 8. However, the determination of the breast contact area in step S1b is different from the embodiment in FIG. 8. According to the embodiment in FIG. 9 the breast contact area is determined by estimating the breast size in a pre-compressed state. I.e. the breast is positioned on a support plate 15 (FIG. 11) and a minimal compression force of for example 50 N is applied to the breast by a compression plate 3 (FIG. 11). For the estimation of the breast contact area visual markers 17 as for example shown in FIG. 13 may be printed onto the compression plate 3 and/or onto the support plate 15. Alternatively, the visual markers 17 may be projected onto the plates 3, 15 by a projector 37 (FIG. 11) such as for example by a laser.

The estimated breast contact area is not entered into the system. The compression force limit is determined continuously in step S5 for each possible breast size. After the start of the compression initiated by an AMT in step S7 the output signal is provided on the display 27 in step S9b. Therein, the output signal indicates for which breast size the currently applied force is ok. I.e. for which breast size the currently applied compression force does not cause excessive pain. The AMT may combine his knowledge of the estimated breast size with the output signal and decide in step S11 to complete or to continue the application of compression force.

A further embodiment of a method is shown in FIG. 10. Contrary to the embodiments described with respect to FIGS. 8 and 9 the breast contact area is determined automatically by the system by directly measuring the breast contact area on the compression plate 3 or on the support plate 15 (step S1c). Therein, automatically may denote that the breast contact area is determined without user interaction after a breast is placed between the support plate 15 and the compression plate 3. For determining the breast contact area the mammography system 7 may employ visual markers 17 as described with respect to FIG. 9 above and FIG. 13 below. The visual markers 17 may indicate breast contours of a certain breast size. Each indicated breast contour may be associated with a discrete compression force limit. The system 7 may correlate the smallest contour that completely surrounds the breast contact area to a current compression state. The breast contact area may be measured by a tracking device 23 such as optical cameras as shown in FIG. 11.

For each of the visual markers 17 a compression force limit is determined in step S5. To facilitate the compression procedure, in addition to the display of an optical output signal, acoustical signals are triggered whenever the applied compression force exceeds the compression force limit or threshold between two neighboring breast size categories. According to an embodiment the frequency and/or tone pitch of the acoustic signal varies with the different breast size categories.

Further, the method described in FIG. 10 may correspond to the embodiment described with respect to FIG. 8. However, the output signal in FIG. 10 is provided in step S9c indicating whether the applied compression force is low, ok or high based on the measured breast contact area.

According to a further embodiment of the invention the radiology assistant or AMT remains in full control of the compression procedure. The proposed embodiments only provide an objective discomfort indicator thereby enabling the user to stop or change the compression when the breast is compressed enough for obtaining good image quality. At the same time it is possible to reduce discomfort for the person under examination.

FIG. 11 schematically shows a system 7 for individually monitoring a compression force and for providing a possibility for optimization of the compression force during a mammographic examination according to an embodiment of the invention. The system 7 comprises a support plate 15 for supporting a breast while radiographic images are obtained and a compression plate 3 for compressing the breast between the support plate 15 and the compression plate 3 while the radiographic images are obtained. One of the compression plate 3 and the support plate 15 may be designed movable with relation to the other plate. A breast under examination may be positioned between the support plate 15 and the compression plate 3 such that the support plate 15 is below and the compression plate 3 above the breast. The compression plate 3 and the support plate 15 are part of an apparatus 9 for mammographic examinations.

The system 7 furthermore comprises a monitoring device 19 which may be part of a processing unit 31. The monitoring device 19 may be connected wirelessly or by cables (not shown in FIG. 11) to several components of the system 7. For example, the monitoring device 19 may be connected to a screen or display 27, an interaction device 25 also denoted as interface unit, a tracking device 23, a force sensor 21, an X-ray source 11, an X-ray detector 13, an adjusting mechanism 29, an adjustable support 35 and a projector 37. The monitoring device 19 is adapted for determining a breast contact area A between the breast and the compression plate 3 or between the breast and the support plate 15. Furthermore, the monitoring device 19 is adapted for determining a compression force limit F based on the determined breast contact area A. Therein, the monitoring device 19 may calculate the compression force limit F according to a pressure-force optimization rule or alternatively derive a compression force limit F corresponding to a certain breast size category from a memory or from a data base. Moreover, the monitoring device 19 is adapted for providing an output signal 5 representative of the relation between the breast contact area A and the force limit F for example to the display 27.

According to a further embodiment the system 7 comprises an X-ray imaging system for acquiring radiographic images of the breast. The Imaging system comprises an X-ray source 11 and an X-ray detector 13. The example shown in FIG. 11 is a so-called stand-up investigation system where, for example, a patient in an upright position can stand while, for example, the breast is examined.

Therefore, the X-ray detector 13 is provided as a sort of a paddle or small table upon which a breast can be received. Thus, the X-ray detector 13 may be positioned under the support plate 15 or be integrated into the support plate 15. The moveable compression plate 3 is provided with an adaptable distance D to the X-ray detector 13 in order to be able to act with a desired pressing force on the breast. The compression plate 3 is attached to an adjusting mechanism 29 allowing the necessary movement of the compression plate 3.

The X-ray source 11 generates X-ray radiation emanating towards the detector 13. Therefore, the compression plate 3 is designed X-ray transparent. The X-ray source 11 and the X-ray detector 13 are attached to an adjustable support 35 allowing for a vertical adjustment such that the height of the X-ray detector 13 may be adapted to different sizes of the person under examination. A rotational movement of the imaging system is possible to acquire X-ray images not only in a vertical direction, but also in a direction with an angle to the vertical direction, such as for example 30° or an X-ray viewing direction in a horizontal way. A base 33 is provided which is for example securely fixed to a floor of an examination room.

Figure 12:
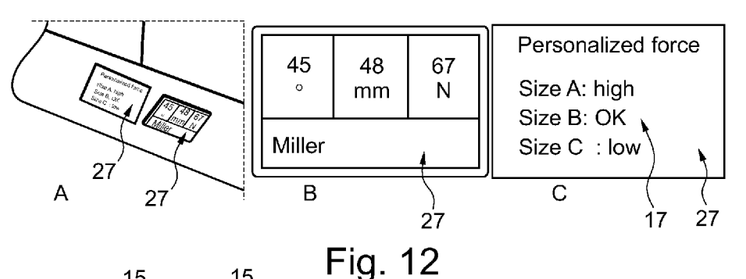
FIG. 12 shows different possibilities for providing a visual output signal according to an embodiment of the invention

According to a further embodiment of the invention the system 7 further comprises a display 27 adapted for displaying the output signal 5. The display device 27 may include optical and acoustical means. The display 27 may be provided as a separate device and/or for example be included into the base 33 of the system 7. Furthermore, several displays 27 may be provided as shown in FIG. 11. Possible display embodiments are shown in FIG. 12. The display 27 may be connected to a processing unit 31, and in particular to a monitoring device 19. Moreover, the display 27 may be connected to an interaction device 25 such as a keyboard. Alternatively, the display 27 may include the interaction device 25 for example in form of a touch screen. The interaction device 25 may serve for example for a manual input of the breast contact area into the monitoring device 19.

It must be noted that the X-ray imaging system shown is a so-called stand type. It is further noted that the present invention also comprises other types for X-ray imaging, for example moveable or stationary X-ray imaging systems or X-ray imaging systems with a table upon which a patient can be received in order to acquire X-ray images while the patient is lying on the table, for example facing downwards.

According to a further embodiment of the invention, the mammography image data is based on CT data acquired by the X-ray image acquisition device, for example by a CT image acquisition system.

According to a further embodiment of the invention the system 7 comprises a tracking device 23 for measuring the breast contact area A in real time. For example, the tracking device 23 may be arranged above the breast and above the compression plate 3. The tracking device 23 may be a system of optical cameras which acquire the breast contact area A for example in combination with visual markers 17 described in the embodiment of FIG. 13. The measured breast contact area value may be provided by the tracking device 23 to the monitoring device 19 where a compression force limit F is determined based on the measured breast contact area as described in the embodiment of FIG. 10.

According to a further embodiment of the invention the system 7 comprises a force sensor 21 which measures the currently applied compression force and provides the measured values to the monitoring device 19. In this way the current compression force may be compared to a previously determined compression force limit.

According to a further embodiment of the invention the system 7 comprises a projector 37 which for example may be arranged above the breast and above the compression plate 3. The projector 37 may be adapted for projecting visual markers 17 onto one of the plates 3, 15 for facilitating the determination of the breast contact area. In the embodiment presented in FIG. 11 the visual markers 17 are provided on the compression plate 3.

FIG. 12 shows different possibilities for providing a visual output signal according to an embodiment of the invention. FIG. 12A shows the design of the display 27 which comprises two output areas. The output signal 5 may be provided on a display 27 arranged at the processing unit 31. Alternatively or additionally the output signal 5 may be provided on a display 27 at the base 33 of system 7. The display 27 may for example be a liquid crystal display (LCD). FIG. 12B shows a first output area where for example the name of the person under examination, the currently applied compression force, the angle of the image acquisition system and the current breast contact area are displayed. FIG. 12C shows a second output area where for example the output signal 17 is presented. As described in connection with the embodiment in FIG. 9 the output signal 17 indicates for which breast size the currently applied compression force is adequate. In the example shown the currently applied compression force is "high" for breasts of the breast size category A, "ok" for breasts of the breast size category B, and "low" for breasts of the breast size category C.

According to a further embodiment of the invention the output signal 17 is enhanced by colours. For example, the term "high" may be displayed in blue or red colour, the term "ok" in green colour and the term "low" in black colour.

Figure 13:
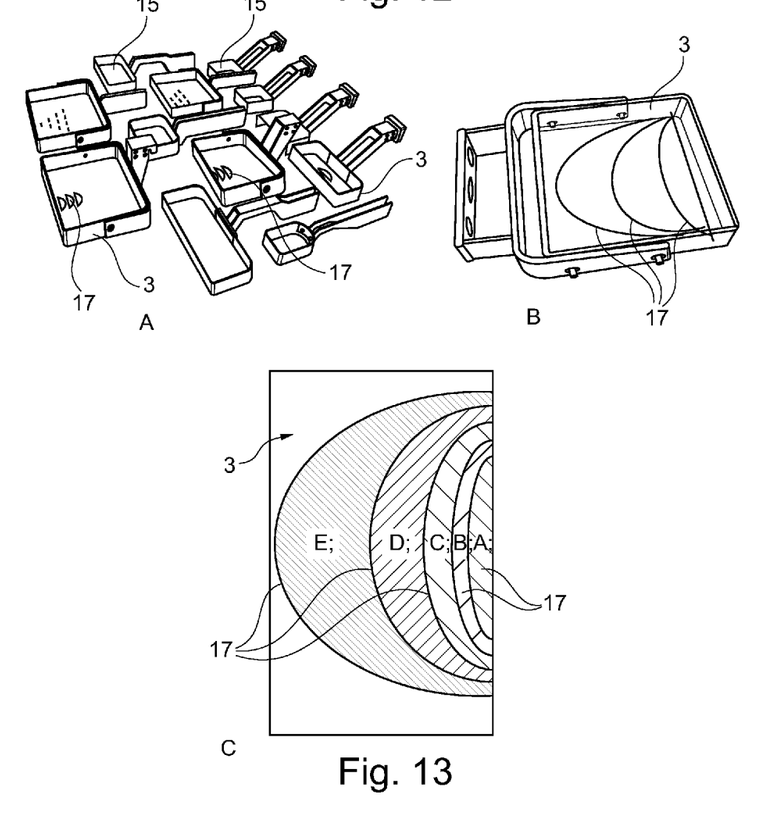
FIG. 13 shows different possibilities for determining the breast contact area according to an embodiment of the invention

In FIG. 13 different embodiments of the compression plate 3 and/or of the support plate 15 are shown. The plates 3, 15 are provided with visual markers 17 which facilitate the estimation or measurement of the breast contact area. In FIGS. 13A and 13B the visual markers 17 are provided permanently on the plates 3, 15. In the embodiment of FIG. 13C the visual markers 17 are projected onto the plates 3, 15 for example by a laser.

FIG. 13A shows different embodiments of compression plates 3 and support plates 15. The plates 3, 15 are provided as paddles. In FIG. 13B a bigger representation of a compression plate 3 is shown. The visual markers 17 on the compression plate 3 show three different breast size categories.

In FIG. 13C visual markers 17 are projected in different colours for each breast size category. For example, the overall area for placing the breast on the compression plate 3 or on the support plate 15 may be 24 by 30 cm. Thus, the overall area may for example correspond to 720 cm² and have blue colour. Areas representing different breast sizes are projected in red, yellow, green, orange, and/or any further colour by a projector 37 onto the plate 3, 15. The area representing an A size breast may be 36 cm², the area representing an B size breast 72 cm², the area representing an C size breast 144 cm², the area representing an D size breast 288 cm² and the area representing an E size breast 576 cm². The breast sizes may be correlated by a factor of 2 in breast contact area.

When laser markers are used, the initial light marker can be manually adjusted to the shape of the slightly pre-compressed breast and a first compression limit may be computed for the initial breast state. Additional breast contours may be computed from the initial contour and may be projected onto the compression plate 3 and/or onto the support plate 15 with the corresponding values of the compression force limits.

According to a further embodiment of the invention a computer program or a computer program element is provided that is characterized by being adapted to execute the method steps of the method according to one of the preceding embodiments, on an appropriate system.

The computer program element might therefore be stored on a computer unit, which might also be part of an embodiment of the invention. This computing unit may be adapted to perform or induce a performing of the steps of the method described above. Moreover, it may be adapted to operate the components of the above described system or apparatus. The computing unit can be adapted to operate automatically and/or to execute the orders of a user. A computer program may be loaded into a working memory of a data processor. The data processor may thus be equipped to carry out the method of the invention.

This embodiment of the invention covers both, a computer program that right from the beginning uses the invention and a computer program that by means of an up-date turns an existing program into a program that uses the invention.

Furthermore, the computer program element may be adapted for providing all necessary steps to fulfil the procedure of an exemplary embodiment of the method as described above.

According to a further embodiment of the invention a computer readable medium, such as a CD-ROM, is presented wherein the computer readable medium has a computer program element stored on it which computer program element is described by the preceding section.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device or system type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 3 compression plate (movable)
5 output signal
7 system for monitoring a compression force
9 apparatus for mammographic examination
11 X-ray source
13 X-ray detector
15 support plate
17 visual markers
19 monitoring device
21 force sensor
23 tracking device (optical cameras)
25 interaction device (interface unit)
27 display
29 adjusting mechanism
31 processing unit
33 base
35 adjustable support
37 projector
F compression force exerted on a breast
A breast contact area
p pressure excreted on the
S1a determining a breast contact area by estimating the breast size
S1b determining a breast contact area by estimating the breast size in a pre-compressed state
S1c determining a breast contact area automatically by measuring
S3 providing the estimated breast size to the system
S5 determining a compression force limit based on the breast contact area
S7 starting a compression of the breast
S9a providing an output signal by indicating on a display whether the applied compression force is low, ok or high for the entered breast size S9b providing an output signal by indicating on a display for which breast size the currently applied force is ok S9c providing an output signal by indicating on a display whether the applied compression force is low, ok or high for the measured breast size S11 MTA decides to complete or to continue the compression of the breast

The invention claimed is:

1. A method for individually monitoring a compression force (F) in an apparatus for mammographic examination, the method comprising:
   determining a breast contact area between (A) a breast under examination and a compression plate or a support plate;
   determining a compression force limit based on the breast contact area (A), wherein the compression force limit is directly proportional to a mathematical function of the breast contact area; and
   providing an output signal representative of the relation between the breast contact area (A) and the compression force limit.

2. The method according to claim 1,
   wherein the compression force limit is proportional to one of the following mathematical functions of the breast contact area: a logarithm function, an exponential function, a power function and a linear function.

3. The method according to claim 2,
   wherein the compression force limit is proportional to a combination of at least two of the mathematical functions of the breast contact area.

4. The method according to claim 1,
   wherein the determined breast contact area (A) is correlated to a breast size; and
   wherein for each breast size a discreet compression force limit is determined.

5. The method according to claim 1,
   wherein the breast contact area (A) is determined by estimating the breast size by a user before the compression of the breast.

6. The method according to claim 1,
   wherein the breast contact area (A) is determined automatically in real-time during the compression of the breast.

7. The method according to claim 1,
   wherein the output signal is an optical and/or an acoustical signal.

8. The method according to claim 1,
   wherein the output signal is provided when the compression force limit is reached during the mammographic examination.

9. The method according to claim 7,
   wherein the acoustical signal varies in frequency and/or tone depending on the breast size correlated to the compression force limit.

10. A system for individually monitoring a compression force (F) during a mammographic examination, the system comprising
    a support plate for supporting a breast while radiographic images are obtained;
    a compression plate for compressing the breast between the support plate and the compression plate while the radiographic images are obtained;
    a monitoring device for monitoring a compression force (F) applied to the breast,
    the monitoring device being adapted to: determine a breast contact area (A) between the breast and the compression plate or between the breast and the support plate;
    determine a compression force limit based on the determined breast contact area (A), wherein the compression force limit is directly proportional to a mathematical function of the breast contact area; and
    to provide an output signal representative of the relation between the breast contact area (A) and the force limit.

11. The system according to claim 10, further comprising a tracking device for measuring the breast contact area (A) in real time and for providing the measured breast contact area to the monitoring device.

12. The system according to claim 10, further comprising an interaction device for manual input of the breast contact area (A) into the monitoring device.

13. The system according to claim 10,
    wherein visual markers are provided on the compression plate (3) or on the support plate for determining the breast contact area (A).

14. A tangible non-transitory computer readable storage medium that stores a computer program element, the computer program element, when executed by a processor, causes the processor to control the a system of claim 10.

15. The method according to claim 1, wherein the mathematical function is a logarithmic function.

16. The system according to claim 10, wherein the mathematical function is a logarithmic function.

* * * * *